US012589110B2

(12) United States Patent
Harada et al.

(10) Patent No.: US 12,589,110 B2
(45) Date of Patent: Mar. 31, 2026

(54) CARBONATED AEROSOL EXTERNAL PREPARATION FOR SKIN

(71) Applicant: KAO CORPORATION, Tokyo (JP)

(72) Inventors: Ryoko Harada, Funabashi (JP);
Tadashi Miyazaki, Sumida-ku (JP);
Megumi Matsuoka, Katsushika-ku (JP)

(73) Assignee: KAO CORPORATION, Tokyo (JP)

( * ) Notice: Subject to any disclaimer, the term of this patent is extended or adjusted under 35 U.S.C. 154(b) by 448 days.

(21) Appl. No.: 18/247,598

(22) PCT Filed: Oct. 1, 2021

(86) PCT No.: PCT/JP2021/036412
§ 371 (c)(1),
(2) Date: Mar. 31, 2023

(87) PCT Pub. No.: WO2022/071575
PCT Pub. Date: Apr. 7, 2022

(65) Prior Publication Data
US 2023/0372387 A1      Nov. 23, 2023

(30) Foreign Application Priority Data

Oct. 2, 2020    (JP) ................................. 2020-167996

(51) Int. Cl.
| | |
|---|---|
| *A61K 31/727* | (2006.01) |
| *A61K 9/00* | (2006.01) |
| *A61K 9/12* | (2006.01) |
| *A61K 47/02* | (2006.01) |
| *A61K 47/32* | (2006.01) |
| *A61K 47/40* | (2006.01) |

(52) U.S. Cl.
CPC .......... *A61K 31/727* (2013.01); *A61K 9/0014* (2013.01); *A61K 9/122* (2013.01); *A61K 47/02* (2013.01); *A61K 47/32* (2013.01); *A61K 47/40* (2013.01)

(58) Field of Classification Search
CPC .............................. A61K 31/737; A61K 9/124
See application file for complete search history.

(56) References Cited

U.S. PATENT DOCUMENTS

2019/0133894 A1      5/2019   Kobayashi et al.

FOREIGN PATENT DOCUMENTS

| | | |
|---|---|---|
| EP | 3 831 359 A1 | 6/2021 |
| JP | 2002-020294 A | 1/2002 |
| JP | 2009-269914 A | 11/2009 |
| JP | 2013-224275 A | 10/2013 |
| JP | 2015-221783 A | 12/2015 |
| JP | 5986394 B2 | 9/2016 |
| JP | 2016-180012 A | 10/2016 |
| JP | 2017-154991 A | 9/2017 |
| JP | 2018-43932 A | 3/2018 |
| JP | 2019-172703 A | 10/2019 |
| JP | 2020-19784 A | 2/2020 |
| WO | WO 2020/027177 A1 | 2/2020 |
| WO | WO 2020/138403 A1 | 7/2020 |

OTHER PUBLICATIONS

Oh, AAPS PharmSciTech, vol. 16, No. 2, Apr. 2015. (Year: 2015).*
International Search Report issued Dec. 7, 2021 in PCT/JP2021/036412, filed on Oct. 1, 2021, 2 pages.
Extended European Search Report issued Sep. 23, 2024 in European Patent Application No. 21875871.2, 8 pages.

* cited by examiner

*Primary Examiner* — Layla D Berry
(74) *Attorney, Agent, or Firm* — Oblon, McClelland, Maier & Neustadt, L.L.P.

(57) ABSTRACT

A carbonated aerosol external preparation for skin, including a stock solution containing the following components (A) to (C), and a propellant containing the following component (D): (A) heparinoid, (B) water-soluble polymer, (C) water, and (D) carbon dioxide gas. The carbonated aerosol external preparation for skin has a pH immediately after discharge of 4.0 or more and 7.0 or less. The component (B) includes one or more selected from the group consisting of hydroxypropylmethylcellulose and acrylic acid/alkyl (meth)acrylate copolymer. A content of the component (B) in the stock solution is from 0.05 to 5.0% by mass, based on a total mass of the stock solution.

16 Claims, No Drawings

CARBONATED AEROSOL EXTERNAL PREPARATION FOR SKIN

CROSS REFERENCE TO RELATED APPLICATIONS

This application is a National Stage entry under 35 U.S.C. § 371 of PCT/JP2021/036412, filed on Oct. 1, 2021, and claims priority to Japanese Patent Application No. 2020-167996, filed on Oct. 2, 2020. The entire contents of both are incorporated herein by reference.

FIELD OF THE INVENTION

The present invention relates to a carbonated aerosol external preparation for the skin.

BACKGROUND OF THE INVENTION

Heparinoid includes various hydrophilic groups such as a sulfate group, a carboxyl group and a hydroxyl group in the structure, and has pharmacological effects such as moisturizing effects and anti-inflammatory effects. External preparations for the skin containing heparinoid are effective for the treatment and the prevention of thrombophlebitis (including hemorrhoid), pain and inflammatory diseases caused by vascular insufficiency (including induration and pain after injection), chilblain, hypertrophic scar and keloid, keratodermia tylodes palmaris progressiva, asteatosis, and swelling, hematoma, tenosynovitis, myalgia and arthritis after injury (bruise, distortion, contusion), and torticollis muscularis (in infancy).

Commercially available dosage forms of heparinoid-containing external preparations for the skin include cream, soft ointment, lotion and foam spray. Of these dosage forms, foam spray is expected to prevent dripping at the affected site compared to lotion, and is easier to spread on the affected site than cream or ointment. For example, Patent Literature 1 discloses a composition for screen foamer comprising heparinoid, a non-ionic surfactant and a specific polyol, which can form bubbles by screen foamer without using any gas for forming bubbles in consideration of irritancy to the skin due to liquefied natural gas. Furthermore, Patent Literature 2 discloses a foaming composition comprising a stock solution which contains heparinoid and a specific nonionic surfactant and does not contain lower alcohol, and a propellant.

Meanwhile, carbon dioxide gas is known to have the effect of promoting blood circulation and hyperthermia effect, and aerosol cosmetic using carbon dioxide gas as a propellant has been used (e.g., Patent Literature 3).

PATENT LITERATURES

Patent Literature 1: JP-A-2019-172703
Patent Literature 2: JP-A-2016-180012
Patent Literature 3: JP-A-2018-43932

SUMMARY OF THE INVENTION

The present invention provides a carbonated aerosol external preparation for the skin, comprising a stock solution comprising the following components (A) to (C) and a propellant comprising a component (D):
  (A) heparinoid
  (B) water-soluble polymer
  (C) water
  (D) carbon dioxide gas, wherein the carbonated aerosol external preparation for the skin has a pH immediately after discharge of 4.0 or more and 7.0 or less.

DETAILED DESCRIPTION OF THE INVENTION

The composition for screen foamer disclosed in Patent Literature 1 is difficult to form fine bubbles, and when the composition is applied on the skin, a friction may be felt on the skin. Furthermore, since LPG is used as a propellant in the foaming composition disclosed in Patent Literature 2, the problem is that the composition is irritating to the skin.

Meanwhile, the surface of the human skin is kept weakly acidic in order to maintain homeostasis, but a dry, inflamed skin, for which an external preparation for the skin containing heparinoid is to be used, is known to have a higher pH. To repair such skin, application of a weakly acidic preparation is important, but bubbles discharged in the compositions disclosed in Patent Literatures 1 and 2 have a pH in the neutral region, which is higher than the pH of the weakly acidic skin. Addition of a large amount of pH adjustor to make the preparation weakly acidic to improve buffering ability, however, results in skin irritation and tight skin. To deal with this, use of carbon dioxide gas as a propellant as in the cosmetic disclosed in Patent Literature 3 allows pH to be adjusted to weakly acidic while suppressing skin irritation and tight skin. However, it has been found that the preparation loses carbonation after discharge and then the pH is increased close to neutral. It is also desired to reduce friction when the preparation is applied to and spread on the skin to suppress physical irritation to the skin.

The present inventors found that the above problem can be solved by using carbon dioxide gas as a propellant and including a water-soluble polymer in a stock solution together with heparinoid.

The carbonated aerosol external preparation for the skin of the present invention can avoid skin irritation and tight skin, is easy to spread and can be kept weakly acidic even after discharge.

Stock Solution

The stock solution in the carbonated aerosol external preparation for the skin of the present invention comprises the following components (A) to (C).

[Component (A): Heparinoid]

Heparinoid of the component (A) is also called mucopolysaccharide polysulfuric acid ester, which is prepared by polysulfating mucopolysaccharide with a repeating unit of disaccharide composed of D-glucuronic acid and N-acetyl-D-galactosamine. Heparinoids listed in the Japanese Pharmaceutical Codex 2002 are preferred as the heparinoid.

The average molecular weight of heparinoid is not particularly limited, and heparinoid has an average molecular weight of preferably 1,000 to 1,000,000 Mw and particularly preferably 5,000 to 100,000 Mw from the viewpoint of drug efficacy including moisturizing action. The amount of the organic sulfuric acid group (%) in heparinoid is not particularly limited, and is preferably 20 to 40%, and more preferably 25 to 38% from the viewpoint of drug efficacy including moisturizing action. The amount of the organic sulfuric acid group is measured by the method described in the section of "Heparinoid" in the Japanese Pharmaceutical Codex 2002.

The content of the component (A) in the stock solution is preferably 0.05% by mass or more, more preferably 0.07% by mass or more and further preferably 0.1% by mass or more, and preferably 0.6% by mass or less, more preferably 0.5% by mass or less and further preferably 0.4% by mass or less from the viewpoint of drug efficacy including moisturizing action and use impression. The content of the component (A) in the stock solution is in a specific range of preferably 0.05 to 0.6% by mass, more preferably 0.07 to 0.5% by mass and further preferably 0.1 to 0.4% by mass.

[Component (B): Water-Soluble Polymer]

The water-soluble polymer of the component (B) is not particularly limited as long as it is used for usual external preparation for the skin. Examples thereof include a plant polymer, a microorganism polymer, mucopolysaccharide, a cellulose polymer, a starch polymer, a vinyl polymer, an acrylic polymer and a polyoxyethylene polymer. It is preferable that the water-soluble polymer of the component (B) has a weight average molecular weight of 10,000 or more. The weight average molecular weight is measured by using gel permeation chromatography (GPC)—multiangle laser light scattering detection system (MALLS) with polyethylene oxide as the reference material.

The component (B) has a viscosity in 2% by mass aqueous solution at 20° C. of preferably 5 mPa·s or more, more preferably 10 mPa·s or more and further preferably 20 mPa·s or more in order to keep the preparation after discharge weakly acidic. The component (B) has a viscosity in 2% by mass aqueous solution at 20° C. of preferably 100,000 mPa·s or less, more preferably 8,000 mPa·s or less and further preferably 5,000 mPa·s or less in order to improve discharge properties. The viscosity is measured by a B-type viscometer (e.g., VISCOMETER TVB10 made by Toki Sangyo Co., Ltd.) at 20° C.

Examples of plant polymers include gum arabic, locust bean gum, guar gum, karaya gum, carrageenan, pectin, agar and starch (rice, corn, potatoes and wheat). Examples of microorganism polymers include xanthan gum and gellan gum. Examples of mucopolysaccharides include hyaluronic acid, tuberose polysaccharide and Tremella fuciformis polysaccharide. Examples of cellulose polymers include methylcellulose, ethylcellulose, carboxymethylcellulose, hydroxymethylcellulose, hydroxyethylcellulose, hydroxypropylcellulose, hydroxypropylmethylcellulose, hydroxypropylmethylcellulose stearoxy ether, nitrocellulose, cellulose sodium sulfate, carboxymethylcellulose sodium salt, crystalline cellulose, cellulose powder and hydroxyethylcellulose hydroxypropyl stearyl ether hydroxypropyl sodium sulfonate. Examples of starch polymers include carboxymethyl starch and methylhydroxypropyl starch. Examples of vinyl polymers include polyvinylmethyl ether, polyvinyl pyrrolidone and carboxyvinyl polymer. Examples of acrylic polymers include sodium polyacrylate, polyethyl acrylate, polyacrylic acid amide, acrylic acid/alkyl (meth)acrylate copolymer, (Na acrylate/acryloyl dimethyltaurine Na) copolymer, polyacrylate crosspolymer-6 and 2-methacryloyloxyethyl phosphorylcholine/butyl methacrylate copolymer. Examples of polyoxyethylene polymers include polyethylene oxide.

Of them, water-soluble polymers with a sugar backbone, such as a plant polymer, a microorganism polymer, mucopolysaccharide, a cellulose polymer and a starch polymer are preferred in order to keep the preparation after discharge weakly acidic and to reduce friction in application; cellulose polymers are more preferred, and hydroxypropylmethylcellulose, hydroxypropylmethylcellulose stearoxy ether and hydroxyethylcellulose are further preferred.

The content of the component (B) in the stock solution is preferably 0.01% by mass or more, more preferably 0.05% by mass or more, further preferably 0.10% by mass or more and further more preferably 0.20% by mass or more, and preferably 5.0% by mass or less, more preferably 2.0% by mass or less, further preferably 1.0% by mass or less and further more preferably 0.80% by mass or less in order to keep the preparation after discharge weakly acidic and to reduce friction in application. The content of the component (B) in the stock solution is in a specific range of preferably 0.01 to 5.0% by mass, more preferably 0.05 to 2.0% by mass, further preferably 0.10 to 1.0% by mass and further more preferably 0.20 to 0.80% by mass.

The mass ratio of the component (A) to the component (B), (A)/(B), in the stock solution is preferably 0.01 or more, more preferably 0.03 or more and further preferably 0.1 or more, and preferably 60 or less, more preferably 10 or less and further preferably 4 or less to improve homogeneity of the preparation and improve its use impression when applied and spread. The mass ratio of the component (A) to the component (B), (A)/(B), in the stock solution is in a specific range of preferably 0.01 to 60, more preferably 0.03 to 10, and further preferably 0.1 to 4.

[Component (C): Water]

The content of the component (C), water, in the stock solution is preferably 10° by mass or more, more preferably 20% by mass or more and further preferably 40% by mass or more, and preferably 90% by mass or less, more preferably 85% by mass or less and further preferably 80% by mass or less from the viewpoint of penetration to the skin of the preparation discharged and solubility of heparinoid and other components. The content of the component (C) in the stock solution is in a specific range of preferably 10 to 90% by mass, more preferably 20 to 85% by mass, and further preferably 40 to 80% by mass.

[Component (E): Specific pH Adjustor]

The stock solution may further contain one or more pH adjustors selected from the group consisting of an organic acid, an organic acid salt, an amino acid, an amino acid salt, an amine, an inorganic acid, an inorganic acid salt and an inorganic base. Examples of organic acids include glycolic acid, citric acid, malic acid, succinic acid, tartaric acid and lactic acid. Examples of salts thereof include potassium salts and sodium salts. Examples of amino acids include glutamic acid, aspartic acid, arginine and lysine. Examples of salts thereof include sodium salts, hydrochloride and succinate. Examples of amines include aliphatic amines such as monoethanolamine, triethanolamine, methylamine, ethylamine, trimethylamine, triethylamine, ethylenediamine and tetramethylethylenediamine. Examples of inorganic acids include phosphoric acid, and examples of inorganic acid salts include potassium dihydrogenphosphate and disodium hydrogenphosphate. Examples of inorganic bases include alkali metal hydroxides such as lithium hydroxide, sodium hydroxide and potassium hydroxide. Of them, organic acid, organic acid salt, amino acid, amino acid salt, amine and inorganic base are preferred from the viewpoint of the improvement of stability of heparinoid.

The content of the component (E) in the stock solution is preferably 0.01% by mass or more, more preferably 0.05% by mass or more and further preferably 0.1% by mass or more from the viewpoint of stability of heparinoid, and preferably 0.7% by mass or less, more preferably 0.5% by mass or less and further preferably 0.4% by mass or less from the viewpoint of reduction of skin irritancy and tight skin. The content of the component (E) in the stock solution is in a specific range of preferably 0.01 to 0.7% by mass, more preferably 0.05 to 0.5% by mass and further preferably 0.1 to 0.4% by mass.

The mass ratio of the component (A) to the component (E), (A)/(E), in the stock solution is preferably 0.05 or more, more preferably 0.1 or more and further preferably 0.2 or more, and preferably 60 or less, more preferably 10 or less and further preferably 4 or less from the viewpoint of reduction of skin irritancy and tight skin. The mass ratio of the component (A) to the component (E), (A)/(E), in the stock solution is in a specific range of preferably 0.05 to 60, more preferably 0.1 to 10 and further preferably 0.2 to 4.

The mass ratio of the component (B) to the component (E), (B)/(E), in the stock solution is preferably 0.01 or more, more preferably 0.1 or more and further preferably 0.2 or more, and preferably 500 or less, more preferably 40 or less and further preferably 2.5 or less in order to keep the preparation after discharge weakly acidic. The mass ratio of the component (B) to the component (E), (B)/(E), in the stock solution is in a specific range of preferably 0.01 to 500, more preferably 0.1 to 40 and further preferably 0.2 to 2.5.

The mass ratio of the component (D) to the component (E), (D)/(E), in the stock solution is preferably 0.01 or more, more preferably 0.2 or more, further preferably 2.5 or more, further more preferably 3.0 or more, and yet more preferably 3.5 or more from the viewpoint of reduction of skin irritancy and tight skin, and preferably 500 or less, more preferably 60 or less, further preferably 30 or less, further more preferably 15 or less and yet more preferably 10 or less from the viewpoint of stability of heparinoid. The mass ratio of the component (D) to the component (E), (D)/(E), in the stock solution is in a specific range of preferably 0.01 to 500, more preferably 0.2 to 60, further preferably 2.5 to 30, further more preferably 3.0 to 15 and yet more preferably 3.5 to 10.

[Other Optional Components]

Components usually used for external preparations for the skin may be mixed to the stock solution in addition to the above components. Examples of such components include an oil agent which is liquid at 25° C., polyhydric alcohol, a thickener, a preservative, a powder, ethanol, an antioxidant, a pigment, a perfume, a moisturizing agent, a blood circulation promotor, a cooling agent, an antiperspirant, a fungicide, a whitening agent, an anti-inflammatory agent and a skin activator. These agents may be used for a different purpose regardless of the purpose of use of the agent, or may be used for both the original and different purposes depending on what is intended. For example, antiperspirant may be used as perfume, or may be used as an agent which has the effect of both antiperspirant and perfume.

Polyhydric alcohol usually used for cosmetics may be used as polyhydric alcohol, and examples thereof include divalent alcohol such as ethylene glycol, propylene glycol, propanediol, 1,3-butylene glycol, 1,3-propanediol, dipropylene glycol, polyethylene glycol and polypropylene glycol; and trivalent or higher valent alcohol such as glycerol and sorbitol. Of them, glycerol and divalent polyol are preferred, and glycerol, propylene glycol, propanediol, 1,3-butylene glycol, 1,3-propanediol and dipropylene glycol are more preferred, glycerol, 1,3-propanediol and dipropylene glycol are further preferred, and glycerol and dipropylene glycol are further more preferred from the viewpoint of the improvement of penetration to the skin and uniform applicability of the preparation discharged.

The content of polyhydric alcohol in the stock solution is preferably 1% by mass or more, more preferably 2% by mass or more, further preferably 5% by mass or more and further more preferably 10% by mass or more, and preferably 50% by mass or less, more preferably 40% by mass or less, further preferably 30% by mass or less and further more preferably 20% by mass or less from the viewpoint of the improvement of penetration to the skin and uniform applicability of the preparation discharged. The content of polyhydric alcohol in the stock solution is in a specific range of preferably 1 to 50% by mass, more preferably 2 to 40% by mass, further preferably 5 to 30% by mass and further more preferably 10 to 20% by mass.

Propellant

[Component (D): Carbon Dioxide Gas]

The present invention comprises the component (D), carbon dioxide gas, as a propellant. Carbon dioxide gas and another propellant may also be used in combination as a propellant. Examples of propellants other than carbon dioxide gas include liquefied petroleum gas (ethane, propane, ethylene, isobutane, n-butane, propylene and a mixed gas thereof (e.g. a mixed gas of isobutane and propane, a mixed gas of propane and butane)), an ether propellant (e.g., dimethyl ether), fluorocarbon (e.g., fluorocarbon, chlorofluorocarbon, bromochlorofluoro carbon), compressed gas (e.g., nitrogen, air, a mixed gas thereof), chlorofluorocarbon gas (e.g., monochlorodifluoroethane, tetrafluoroethane). Of them nitrogen, dimethyl ether and liquefied petroleum gas are preferred. When another propellant is used together with carbon dioxide gas of the component (D), any propellant may be used alone, two or more of them may be used in combination.

When a propellant other than carbon dioxide gas of the component (D) is used in combination as a propellant, the ratio of carbon dioxide gas of the component (D) based on the whole propellant is preferably 20% or more, more preferably 40% or more, further preferably 60% or more and further more preferably 80% or more in terms of the volume of gas (1013.25 hPa, 25° C.) so as not to reduce the effect of carbon dioxide gas.

Carbonated Aerosol External Preparation for the Skin

The carbonated aerosol external preparation for the skin of the present invention may be produced by preparing a stock solution comprising the components (A) to (C) and packing it in a pressure resistant container together with a propellant comprising the component (D). The type of spray is preferably a foam type that ejects the preparation in the form of foam.

The ratio of carbon dioxide gas (D) is preferably 0.01 part by mass or more, more preferably 0.10 part by mass or more, further preferably 0.125 part by mass or more, further more preferably 0.25 part by mass or more, yet more preferably 0.5 part by mass or more and yet further preferably 1.0 part by mass or more, and preferably 5.0 parts by mass or less and more preferably 3.0 parts by mass or less based on 100 parts by mass of the stock solution from the viewpoint of improvement of solubility of carbon dioxide gas in the stock solution, the viscosity of foam and spraying properties.

The aerosol external preparation for the skin of the present invention has a pH immediately after discharge of preferably 4.0 or more and 7.0 or less. The pH adjustor of the component (E) described above may be used to adjust the pH to that range. The aerosol external preparation for the skin has a pH immediately after discharge of preferably 4.5 or more and more preferably 5.0 or more, and preferably 6.5 or less and more preferably 6.0 or less. In the present invention, the pH immediately after discharge refers to pH measured 1 minute after discharging the preparation from the aerosol container at 25° C.

When the carbonated aerosol external preparation for the skin of the present invention is a foam type, the foam discharged has a viscosity of preferably 0.1 Pa·s or more, more preferably 0.5 Pa·s or more and further preferably 1.0 Pa·s or more, and preferably 50 Pa·s or less, more preferably 40 Pa·s or less and further preferably 30 Pa·s or less to keep weak acidity. The viscosity of the foam discharged is measured by a B-type viscometer (e.g., VISCOMETER TVB-10 made by Toki Sangyo Co., Ltd.) under conditions of 25° C., rotor No. 3, 12 rpm and 10 seconds.

[How to Use]

The carbonated aerosol external preparation for the skin of the present invention is applied to the skin, more specifically the skin of the whole body excluding the scalp, preferably any one of the face, the body and the limbs, and more preferably the skin of hands and feet in an appropriate amount. The preparation may be dispensed and spread over the hand and applied to the target site, or may be directly discharged to the target site. In the case of a foam type, the preparation may be dispensed and applied to the site so as not to break the foam. It is particularly preferred that the preparation is applied to the site which has thick stratum corneum and can dry up easily, such as hands, feet, fingers, heels elbows and knees. The amount to be applied is approximately 1 g for both hands.

For the embodiments described above, preferred aspects of the present invention will be described in the following.

<1> A carbonated aerosol external preparation for the skin, comprising:

a stock solution comprising the following components (A) to (C); and a propellant comprising the following component (D):

(A) heparinoid (B) water-soluble polymer (C) water (D) carbon dioxide gas, wherein the carbonated aerosol external preparation for the skin has a pH immediately after discharge of 4.0 or more and 7.0 or less.

<2> The carbonated aerosol external preparation for the skin according to <1>, wherein a content of the component (A) in the stock solution is preferably 0.05% by mass or more, more preferably 0.07% by mass or more, and further preferably 0.1% by mass or more, and preferably 0.6% by mass or less, more preferably 0.5% by mass or less, and further preferably 0.4% by mass or less.

<3> The carbonated aerosol external preparation for the skin according to <1> or <2>, wherein the component (B) is preferably one or more selected from a plant polymer, a microorganism polymer, mucopolysaccharide, a cellulose polymer, a starch polymer, a vinyl polymer, an acrylic polymer and a polyoxyethylene polymer, more preferably one or more selected from a water-soluble polymer having a sugar backbone, further preferably one or more selected from a cellulose polymer, and further more preferably one or more selected from hydroxypropylmethylcellulose, hydroxypropylmethylcellulose stearoxy ether and hydroxyethylcellulose.

<4> The carbonated aerosol external preparation for the skin according to any one of <1> to <3>, wherein the component (B) has a viscosity in 2% by mass aqueous solution at 20° C. of preferably 5 mPa·s or more, more preferably 10 mPa·s or more and further preferably 20 mPa·s or more and preferably 100,000 mPa·s or less, more preferably 8,000 mPa·s or less and further preferably 5,000 mPa·s or less.

<5> The carbonated aerosol external preparation for the skin according to any one of <1> to <4>, wherein a content of the component (B) in the stock solution is preferably 0.01% by mass or more, more preferably 0.05% by mass or more, further preferably 0.10% by mass or more and further more preferably 0.20% by mass or more, and preferably 5.0% by mass or less, more preferably 2.0% by mass or less, further preferably 1.0% by mass or less, and further more preferably 0.80% by mass or less.

<6> The carbonated aerosol external preparation for the skin according to any one of <1> to <5>, wherein a mass ratio of the component (A) to the component (B), (A)/(B), in the stock solution is preferably 0.01 or more, more preferably 0.03 or more and further preferably 0.1 or more, and preferably 60 or less, more preferably 10 or less and further preferably 4 or less.

<7> The carbonated aerosol external preparation for the skin according to any one of <1> to <6>, wherein a content of the component (C) in the stock solution is preferably 10% by mass or more, more preferably 20% by mass or more, and further preferably 40% by mass or more, and preferably 90° by mass or less, more preferably 85% by mass or less, and further preferably 80% by mass or less.

<8> The carbonated aerosol external preparation for the skin according to any one of <1> to <7>, wherein the stock solution preferably further comprises one or more pH adjustors selected from the group consisting of an organic acid, an organic acid salt, an amino acid, an amino acid salt, an amine and an inorganic base as a component (E).

<9> The carbonated aerosol external preparation for the skin according to any one of <1> to <8>, wherein a content of the component (E) in the stock solution is preferably 0.01% by mass or more, more preferably 0.05% by mass or more, and further preferably 0.1% by mass or more, and preferably 0.7% by mass or less, more preferably 0.5% by mass or less, and further preferably 0.4% by mass or less.

<10> The carbonated aerosol external preparation for the skin according to <8> or <9>, wherein a mass ratio of the component (A) to the component (E), (A)/(E), in the stock solution is preferably 0.05 or more, more preferably 0.1 or more and further preferably 0.2 or more, and preferably 60 or less, more preferably 10 or less and further preferably 4 or less.

<11> The carbonated aerosol external preparation for the skin according to any one of <8> to <10>, wherein a mass ratio of the component (B) to the component (E), (B)/(E), in the stock solution is preferably 0.01 or more, more preferably 0.1 or more and further preferably 0.2 or more, and preferably 500 or less, more preferably 40 or less and further preferably 2.5 or less.

<12> The carbonated aerosol external preparation for the skin according to any one of <1> to <11>, wherein the stock solution preferably further comprises polyhydric alcohol.

<13> The carbonated aerosol external preparation for the skin according to <12>, wherein polyhydric alcohol preferably comprises one or more selected from glycerol and divalent polyol, more preferably one or more selected from glycerol, propylene glycol, propanediol, 1,3-butylene glycol, 1,3-propanediol and dipropylene glycol, further preferably one or more selected from glycerol, 1,3-propanediol and dipropylene glycol, and further more preferably one or more selected from glycerol and dipropylene glycol.

<14> The carbonated aerosol external preparation for the skin according to <12> or <13>, wherein a content of polyhydric alcohol in the stock solution is preferably 1% by mass or more, more preferably 2% by mass or more, further preferably 5% by mass or more and further more preferably 10% by mass or more, and preferably 50% by mass or less, more preferably 40% by mass or less, further preferably 30% by mass or less and further more preferably 20% by mass or less.

<15> The carbonated aerosol external preparation for the skin according to any one of <1> to <14>, wherein a ratio of the component (D) based on 100 parts by mass of the stock solution is preferably 0.01 part by mass or more, more preferably 0.10 part by mass or more, further preferably 0.125 part by mass or more, further more preferably 0.25 part by mass or more, yet more preferably 0.5 part by mass or more and yet further preferably 1.0 part by mass or more, and preferably 5.0 parts by mass or less and more preferably 3.0 parts by mass or less.

<16> The carbonated aerosol external preparation for the skin according to any one of <1> to <15>, wherein the carbonated aerosol external preparation for the skin has a pH immediately after discharge of preferably 4.5 or more, more preferably 5.0 or more and preferably 6.5 or less.

<17> The carbonated aerosol external preparation for the skin according to any one of <1> to <16>, wherein the preparation is discharged preferably in the form of foam.

EXAMPLES

Examples 1 to 19, Comparative Examples 1 to 4

A stock solution was prepared according to the formulation shown in Tables 1 and 2. The resulting aerosol was put in a pressure-resistant aluminum container together with a propellant (carbon dioxide gas or LPG) to prepare an aerosol skin cosmetic.

For these aerosol skin cosmetics, the ability to maintain pH after discharge, properties of foam and use impression when applied were evaluated by the following methods and the following criteria.

<pH Immediately after Discharge>

The aerosol external preparation for the skin was discharged from the pressure-resistant container under environment of 25° C. and approximately 5 g of the preparation was weighed and put into a 20 mL plastic cup. 1 minute after discharge, the pH was measured by a pH meter (LAQUA F-74).

<Ability to Maintain pH>

The aerosol external preparation for the skin was discharged from the pressure-resistant container and about 5 g of the preparation was weighed and put into a 20 mL plastic cup under an environment of 25° C. The preparation was stirred by a stirrer at 200 rpm for 5 minutes, and then the pH was measured by a pH meter (LAQUA F-74). The difference between the measured value and the pH immediately after discharge was defined as $\Delta$pH, and the ability to maintain pH was rated as follows.

A: $\Delta$pH≤0.5
B: $0.5<\Delta$pH≤1.0
C: $1.0<\Delta$pH≤1.5
D: $1.5<\Delta$pH
X: high pH immediately after discharge <Properties of Foam>

Five expert panelists discharged about 1 g of the aerosol external preparation for the skin from the pressure-resistant container to the palm and scored the appearance of the foam after 10 seconds on a scale of: fine (2 points), rough (1 point) and did not foam (0 point). The sum of the evaluation scores is shown in the tables.

<Use Impression when Applied>

Five expert panelists applied 0.5 g of the aerosol external preparation for the skin discharged from the pressure-resistant container to the forearm and spread it by the palm to which no preparation was applied, and scored the impression on a scale of: smoothly spread on the skin without friction (2 points), moderately smoothly spread on the skin with slight friction (1 point) and difficult to spread on the skin and friction felt. The sum of the evaluation scores is shown in the tables.

<Skin Tightness>

Five expert panelists applied 0.5 g of the aerosol external preparation for the skin discharged from the pressure-resistant container to the forearm and spread it, and scored the touch on the skin 5 minutes after the application on a scale of: not tight at all (2 points), little tight (1 point) and tight (0 point). The sum of the evaluation scores is shown in the table.

TABLE 1

| Composition of stock solution | | Example | | | | | | | | | | Comparative Example | |
|---|---|---|---|---|---|---|---|---|---|---|---|---|---|
| (% by mass, active amount) | | 1 | 2 | 3 | 4 | 5 | 6 | 7 | 8 | 9 | 10 | 1 | 2 |
| (A) | Heparinoid | 0.3 | 0.3 | 0.3 | 0.3 | 0.3 | 0.3 | 0.3 | 0.3 | 0.3 | 0.3 | 0.3 | 0.3 |
| (B) | Hydroxypropyl-methylcellulose (*1) | 0.3 | — | — | — | — | — | — | — | — | — | — | — |
| | Hydroxypropyl-methylcellulose (*2) | — | 0.3 | — | — | — | — | — | — | — | — | — | — |
| | Hydroxypropyl-methylcellulose stearoxy ether (*3) | — | — | 0.3 | — | — | — | — | — | — | — | — | — |
| | Hydroxyethyl-cellulose (*4) | — | — | — | 0.3 | — | — | — | — | — | — | — | — |
| | Polyethylene oxide (*5) | — | — | — | — | 0.3 | — | — | — | — | — | — | — |
| | Sodium carboxy-methylcellulose (*6) | — | — | — | — | — | 0.3 | — | — | — | — | — | — |
| | Carboxyvinyl polymer (*7) | — | — | — | — | — | — | 0.3 | — | — | — | — | — |
| | Acrylic acid/(C10-30) alkyl acrylate copolymer (*8) | — | — | — | — | — | — | — | 0.3 | — | — | — | — |
| | Xanthan gum (*9) | — | — | — | — | — | — | — | — | 0.3 | — | — | — |
| | 2-methacryloyl-oxyethyl phosphorylcholine/ butyl methacrylate copolymer (*10) | — | — | — | — | — | — | — | — | — | 0.3 | — | — |

TABLE 1-continued

| Composition of stock solution | | Example | | | | | | | | | | Comparative Example | |
|---|---|---|---|---|---|---|---|---|---|---|---|---|---|---|
| (% by mass, active amount) | | 1 | 2 | 3 | 4 | 5 | 6 | 7 | 8 | 9 | 10 | 1 | 2 |
| (B') | Polyethylene glycol 200 | — | — | — | — | — | — | — | — | — | — | — | 0.3 |
| (C) | Water | Balance | Balance | Balance | Balance | Balance | Balance | Balance | Balance | Balance | Balance | Balance | Balance |
| (E) | Sodium citrate hydrate | 0.4 | 0.4 | 0.4 | 0.4 | 0.4 | 0.4 | 0.4 | 0.4 | 0.4 | 0.4 | 0.4 | 0.4 |
| | Sodium hydroxide | — | — | — | — | — | — | 0.13 | 0.13 | — | — | — | — |
| Others | Glycerol | 10 | 10 | 10 | 10 | 10 | 10 | 10 | 10 | 10 | 10 | 10 | 10 |
| | Dipropylene glycol | 10 | 10 | 10 | 10 | 10 | 10 | 10 | 10 | 10 | 10 | 10 | 10 |
| Total | | 100 | 100 | 100 | 100 | 100 | 100 | 100 | 100 | 100 | 100 | 100 | 100 |
| Ratio of propellant to stock solution (mass ratio) | | | | | | | | | | | | | |
| stock solution | | 97.8 | 97.8 | 97.8 | 97.8 | 97.8 | 97.8 | 97.8 | 97.8 | 97.8 | 97.8 | 97.8 | 97.8 |
| Propellant | (D) Carbon dioxide gas | 2.2 | 2.2 | 2.2 | 2.2 | 2.2 | 2.2 | 2.2 | 2.2 | 2.2 | 2.2 | 2.2 | 2.2 |
| Total | | 100 | 100 | 100 | 100 | 100 | 100 | 100 | 100 | 100 | 100 | 100 | 100 |
| Ratio | Mass ratio (A)/(B) | 1 | 1 | 1 | 1 | 1 | 1 | 1 | 1 | 1 | 1 | — | — |
| | Mass ratio (A)/(E) | 0.75 | 0.75 | 0.75 | 0.75 | 0.75 | 0.75 | 0.57 | 0.57 | 0.75 | 0.75 | 0.75 | 0.75 |
| | Mass ratio (B)/(E) | 0.75 | 0.75 | 0.75 | 0.75 | 0.75 | 0.75 | 0.57 | 0.57 | 0.75 | 0.75 | 0 | 0 |
| | Mass ratio (D)/(E) | 5.6 | 5.6 | 5.6 | 5.6 | 5.6 | 5.6 | 4.2 | 4.2 | 5.6 | 5.6 | 5.6 | 5.6 |
| pH immediately after discharge | | 5.8 | 5.8 | 5.8 | 5.8 | 5.8 | 5.8 | 5.8 | 5.8 | 5.8 | 5.8 | 5.8 | 5.8 |
| Evaluation | Ability to maintain pH | A | A | A | C | C | C | C | A | B | C | D | D |
| | Properties of foam | 10 | 9 | 10 | 7 | 5 | 4 | 3 | 5 | 6 | 3 | 0 | 0 |
| | Use impression when applied | 10 | 10 | 10 | 7 | 6 | 4 | 4 | 4 | 5 | 3 | 1 | 2 |

TABLE 2

| Composition of stock solution | | Example | | | | | | | | | Comparative Example | |
|---|---|---|---|---|---|---|---|---|---|---|---|---|
| (% by mass, active amount) | | 11 | 12 | 13 | 14 | 15 | 16 | 17 | 18 | 19 | 3 | 4 |
| (A) | Heparinoid | 0.3 | 0.3 | 0.3 | 0.3 | 0.3 | 0.3 | 0.1 | 0.5 | 0.3 | 0.3 | 0.3 |
| (B) | Hydroxypropyl-methylcellulose (*1) | — | 0.2 | 0.45 | 0.8 | 2 | 0.45 | 0.3 | 0.3 | 0.3 | 0.45 | 0.45 |
| | Hydroxypropyl-methylcellulose (*2) | 0.01 | — | — | — | — | — | — | — | — | — | — |
| (C) | Water | Balance | Balance | Balance | Balance | Balance | Balance | Balance | Balance | Balance | Balance | Balance |
| (E) | Sodium citrate hydrate | 0.4 | 0.4 | 0.4 | 0.4 | 0.4 | 0.4 | 0.4 | 0.4 1 | — | 0.4 | 0.4 |
| | Citric acid | — | — | — | — | — | — | — | — | — | — | 0.1 |
| Others | Glycerol | 10 | 10 | 10 | 10 | 10 | 10 | 10 | 10 | 10 | 10 | 10 |
| | Dipropylene glycol | 10 | 10 | 10 | 10 | 10 | 10 | 10 | 10 | 10 | 10 | 10 |
| Total | | 100 | 100 | 100 | 100 | 100 | 100 | 100 | 100 | 100 | 100 | 100 |
| Ratio of propellant to stock solution (mass ratio) | | | | | | | | | | | | |
| stock solution | | 97.8 | 97.8 | 97.8 | 97.8 | 97.8 | 99 | 97.8 | 97.8 | 97.8 | 95.5 | 95.5 |
| Propellant | (D) Carbon dioxide gas | 2.2 | 2.2 | 2.2 | 2.2 | 2.2 | 1 | 2.21 | 2.2 | 2.2 | — | — |
| | LPG | — | — | — | — | — | — | — | — | — | 4.5 | 4.5 |
| Total | | 100 | 100 | 100 | 100 | 100 | 100 | 100 | 100 | 100 | 100 | 100 |
| Ratio | Mass ratio (A)/(B) | 30 | 1.5 | 0.67 | 0.38 | 0.15 | 0.67 | 0.33 | 1.67 | 1 | 0.67 | 0.67 |
| | Mass ratio (A)/(E) | 0.75 | 0.75 | 0.75 | 0.75 | 0.75 | 0.75 | 0.25 | 1.25 | — | 0.75 | 0.6 |
| | Mass ratio (B)/(E) | 0.03 | 0.5 | 1.13 | 2 | 5 | 1.13 | 0.75 | 0.75 | — | 1.13 | 0.9 |
| | Mass ratio (D)/(E) | 5.6 | 5.6 | 5.6 | 5.6 | 5.6 | 2.5 | 5.6 | 5.6 | — | 0.0 | 0.0 |
| pH immediately after discharge | | 5.8 | 5.8 | 5.8 | 5.8 | 5.8 | 5.8 | 5.8 | 5.8 | 4.9 | 7.5 | 5.8 |
| Evaluation | Ability to maintain pH | C | A | A | A | A | A | A | A | A | X | A |
| | Properties of foam | 4 | 8 | 10 | 10 | 10 | 7 | 10 | 10 | 10 | 7 | 6 |
| | Use impression when applied | 4 | 8 | 10 | 10 | 10 | 4 | 10 | 10 | 10 | 3 | 3 |
| | Skin tightness | — | — | 10 | — | — | — | — | — | — | 3 | 2 |

1: METOLOSE 90SH-15000 (made by Shin-Etsu Chemical Co., Ltd.)

2: METOLOSE 60SH-4000 (made by Shin-Etsu Chemical Co., Ltd.)

3: SANGELOSE 90L (made by Daido Chemical Corporation)

4: Natrosol 250HX PHARM (made by Ashland)

5: ALKOX E-100 (made by Meisei Chemical Works, Ltd.)

6: CMC Daicel 1150 (made by DAICEL MIRAIZU Ltd.)

7: Carbopol 980 (made by Lubrizol Advanced Materials)

8: PEMULEN TR-1 (made by Lubrizol Advanced Materials)

9: ECHO GUM T (made by DSP Gokyo Food & Chemical Co., Ltd.)

10: LIPIDURE PMB (made by NOF Corporation)

The invention claimed is:

1. A carbonated aerosol external preparation for skin, comprising:
   a stock solution comprising the following components (A) to (C); and
   a propellant comprising the following component (D):
   (A) a mucopolysaccharide polysulfuric acid ester;
   (B) water-soluble polymer;
   (C) water; and
   (D) carbon dioxide gas,
   wherein the carbonated aerosol external preparation for skin has a pH immediately after discharge of 4.0 or more and 7.0 or less,
   wherein the component (B) comprises one or more selected from the group consisting of hydroxypropylmethylcellulose and acrylic acid/alkyl (meth) acrylate copolymer, and
   wherein a content of the component (B) in the stock solution is from 0.05 to 5.0% by mass, based on a total mass of the stock solution, and
   wherein the carbon dioxide gas is present in the propellant in an amount of 40% or more by volume based on a total gas volume of the propellant at 1013.25 hPa and 25° C.

2. The carbonated aerosol external preparation for skin according to claim 1, wherein a content of the component (A) in the stock solution is from 0.05 to 0.6% by mass, based on a total mass of the stock solution.

3. The carbonated aerosol external preparation for skin according to claim 1, wherein the component (B) has a viscosity in 2% by mass aqueous solution at 20° C. of 5 to 100,000 mPa·s.

4. The carbonated aerosol external preparation for skin according to claim 1, wherein the content of the component (B) in the stock solution is from 0.10 to 2.0% by mass, based on a total mass of the stock solution.

5. The carbonated aerosol external preparation for skin according to claim 1, wherein a mass ratio of the component (A) to the component (B), (A)/(B), in the stock solution is from 0.01 to 60.

6. The carbonated aerosol external preparation for skin according to claim 1, wherein a content of the component (C) in the stock solution is from 10 to 90% by mass, based on a total mass of the stock solution.

7. The carbonated aerosol external preparation for skin according to claim 1, wherein the stock solution further comprises one or more pH adjustors as a component (E) selected from the group consisting of an organic acid, an organic acid salt, an amino acid, an amino acid salt, an amine, and an inorganic base.

8. The carbonated aerosol external preparation for skin according to claim 7, wherein a content of the component (E) in the stock solution is from 0.01 to 0.7% by mass, based on a total mass of the stock solution.

9. The carbonated aerosol external preparation for skin according to claim 7, wherein a mass ratio of the component (A) to the component (E), (A)/(E), in the stock solution is from 0.05 to 60.

10. The carbonated aerosol external preparation for skin according to claim 7, wherein a mass ratio of the component (B) to the component (E), (B)/(E), in the stock solution is from 0.01 to 500.

11. The carbonated aerosol external preparation for skin according to claim 7, wherein the stock solution further comprises a polyhydric alcohol.

12. The carbonated aerosol external preparation for skin according to claim 11, wherein the polyhydric alcohol comprises one or more selected from the group consisting of glycerol and divalent polyol.

13. The carbonated aerosol external preparation for skin according to claim 11, wherein a content of the polyhydric alcohol in the stock solution is from 1 to 50% by mass, based on a total mass of the stock solution.

14. The carbonated aerosol external preparation for skin according to claim 1, wherein a ratio of the component (D) is from 0.01 to 5.0 parts by mass, based on 100 parts by mass of the stock solution.

15. The carbonated aerosol external preparation for skin according to claim 1, wherein the aerosol external preparation for skin has a pH immediately after discharge of 4.5 to 6.5.

16. The carbonated aerosol external preparation for skin according to claim 1, wherein the preparation is discharged in the form of foam.

* * * * *